US008871750B2

(12) United States Patent
Mitwally et al.

(10) Patent No.: US 8,871,750 B2
(45) Date of Patent: Oct. 28, 2014

(54) USE OF AROMATASE INHIBITORS FOR ENDOMETRIAL THINNING IN PREPARATION FOR SURGICAL PROCEDURES ON THE ENDOMETRIAL CAVITY AND UTERUS

(75) Inventors: Mohamed F. M. Mitwally, Bloomfield Hills, MI (US); Michael P. Diamond, Grosse Pointe Shores, MI (US); Robert F. Casper, Toronto (CA)

(73) Assignee: Wayne State University, Detroit, MI (US)

( * ) Notice: Subject to any disclaimer, the term of this patent is extended or adjusted under 35 U.S.C. 154(b) by 694 days.

(21) Appl. No.: 11/661,948

(22) PCT Filed: Oct. 4, 2005

(86) PCT No.: PCT/US2005/035861
§ 371 (c)(1),
(2), (4) Date: Mar. 2, 2007

(87) PCT Pub. No.: WO2006/041939
PCT Pub. Date: Apr. 20, 2006

(65) Prior Publication Data
US 2008/0045484 A1   Feb. 21, 2008

Related U.S. Application Data

(60) Provisional application No. 60/615,978, filed on Oct. 4, 2004.

(51) Int. Cl.
*A61K 31/56* (2006.01)
*A61K 31/4196* (2006.01)
*A61K 31/5685* (2006.01)
*A61K 45/06* (2006.01)

(52) U.S. Cl.
CPC ............ *A61K 31/56* (2013.01); *A61K 31/4196* (2013.01); *A61K 31/5685* (2013.01); *A61K 45/06* (2013.01)
USPC ........................................................ 514/171

(58) Field of Classification Search
USPC ........................................................ 514/171
See application file for complete search history.

(56) References Cited

PUBLICATIONS

Romer et al., European Journal of Obstetrics & Gynecology and Reproductive Biology, 1997;74:201-203.*
Feeley et al., Journal of Clinical Pathology,2001;54(6):435-440.*
Bordie, Semin Oncol., 2003;30(Suppl 14):12-22.*
Buzdar et al., Clinical Cancer Research,2001:7:2620-2635.*
Goss and Strasser, Journal of Clinical Oncology, 2001;19:881-894.*
Dowsett and Haynes, Journal of Steroid Biochemistry & Molecular Biology, 2003;86:255-263.*

* cited by examiner

*Primary Examiner* — San-Ming Hui
(74) *Attorney, Agent, or Firm* — Rohm & Monsanto, PLC

(57) ABSTRACT

Aromatase inhibitors are administered to a female patient prior to endometrial ablation or resection procedures in order to thin the endometrium to a thickness of less than 6 mm, and preferably less than 4 mm, so as to enhance the treatment outcome. Of course, administration of aromatase inhibitors would be useful for other surgical procedures on the endometrial cavity and the uterus. Commercially available aromatase inhibitors, including, the nonsteroidal preparations, anastrozole and letrozole, and a steroidal agent, exemestane, are well-tolerated, and have been shown to decrease serum estrogen levels. The aromatase inhibitor can be used alone, or in combination with other aromatase inhibitors or pharmaceutical agents, such as hormones.

17 Claims, No Drawings

USE OF AROMATASE INHIBITORS FOR ENDOMETRIAL THINNING IN PREPARATION FOR SURGICAL PROCEDURES ON THE ENDOMETRIAL CAVITY AND UTERUS

CROSS-REFERENCE TO RELATED INVENTIONS

This application is a US national stage filing under 35 U.S.C. §371 of International Application No. PCT/US2005/035861 filed on Oct. 4, 2005, and claims the benefit under 35 U.S.C. §119(e) of, U.S. States provisional application Ser. No. 60/615,978 filed on Oct. 4, 2004, the disclosure of which is incorporated herein by reference.

FIELD OF THE INVENTION

This invention relates to a method of medical treatment for endometrial preparation, mainly endometrial thinning, to enhance treatment outcome of endometrial ablation and other surgical procedures on the endometrial cavity and the uterus.

BACKGROUND OF THE INVENTION

Excessive uterine bleeding, menorrhagia, is one of the most common reasons for gynecology referral in pre-menopausal women. Although medical therapy is generally the first approach, many women will eventually require a hysterectomy. Hysterectomy is associated with a significant in-patient hospital stay and a period of convalescence that makes it an unattractive and unnecessarily invasive option for many women. Hysteroscopic endometrial ablation or resection, and more recently "second generation" devices such as balloon or microwave ablation offer a day-case surgical alternative to hysterectomy for these women. These methods are also cheaper procedures than hysterectomy. Hysterectomy guarantees amenorrhea, but is costly and has a significant impact on health-related quality of life immediately after surgery.

Complete endometrial removal or destruction is one of the most important determinants of treatment success. Therefore endometrial ablation will be most effective if undertaken in the immediate post-menstrual phase when endometrial thickness is usually thin (<four mm), the thickness most methods of endometrial ablation are effective in destroying. However there are often difficulties in reliably arranging surgery for this time.

During the menstrual cycle endometrial thickness varies from as little as one mm in the immediate postmenstrual phase to ten mm or more in the late secretary phase. The radius of a standard electrosurgery loop used for endometrial resection is about four mm and the depth of tissue destruction with Nd:YAG laser or a roller ball electrode is four to six mm. With these depths of tissue removal or destruction, it is apparent that surgery will be most effective if undertaken when endometrial thickness is less than 4 mm, either in the immediate post-menstrual phase or following the administration of hormonal agents which induce endometrial thinning or atrophy.

The proportion of women who experience amenorrhea following endometrial ablation varies in different series from 30 to 60%; though the proportion experiencing an improvement in menstrual symptoms is considerably higher.

Difficulty in reliably arranging surgery in the immediate post-menstrual phase and the unpredictable thickness of the unprepared endometrium has resulted in much attention being given to the use of endometrial thinning agents prior to surgery. A number of randomized studies have now been undertaken comparing different hormonal agents with each other or with no pre-operative treatment or placebo. The most commonly evaluated agents have been gonadotropin-releasing hormone (GnRH) agonists and danazol. Progestogens have also been studied.

It has been suggested that the use of these agents, particularly GnRH analogues, will reduce operating time, improve the intra-uterine operating environment, and reduce distension medium absorption. It is also possible that their use may also improve post-operative outcome. An improved operating environment might also reduce the rate of complications associated with these procedures. An improvement in post-operative outcome might increase patient satisfaction and reduce the proportion of women undergoing subsequent hysterectomy. However, these agents do add significant additional cost to any hysteroscopic procedure.

Cost would be one factor that would make the use of progestogens attractive, as they are significantly cheaper than both GnRH analogues and danazol. In a small, randomized study evaluating the effect of progestogens on endometrial thickness alone, norethisterone and medroxyprogesterone acetate had no effect on endometrial thickness, though cyproterone acetate did produce a significant reduction in endometrial thickness in an amount similar to danazol. Observational studies that have included patients treated with different progestogens have reported disappointing effects.

In a recent review article directed to the agents used for endometrial thinning before endometrial ablation, the authors found that when compared with no treatment, GnRH analogues are associated with a shorter duration of surgery, greater ease of surgery, and a higher rate of post-operative amenorrhea at 12 months with hysteroscopic resection or ablation. Post-operative dysmenorrhea also appears to be reduced. However, the use of GnRH analogues was found to have no effect on intra-operative complication rates and patient satisfaction with this surgery. This is because of the high satisfaction rate irrespective of the use of any pre-operative endometrial-thinning agents. GnRH analogues were found to produce more consistent endometrial atrophy than danazol. Both GnRH analogues and danazol produced side effects in a significant proportion of women, though few studies have reported these in detail. Few randomized data are available to assess the effectiveness of progestogens as endometrial thinning agents. The effect of any thinning agent on longer-term results is less certain, but where reported, the effect of endometrial thinning agents on benefits such as post-operative amenorrhea appears to reduce with time.

The reviewers concluded that endometrial thinning prior to hysteroscopic surgery in the early proliferative phase of the menstrual cycle for menorrhagia improves both the operating conditions for the surgeon and short-term post-operative outcome. Gonadotropin-releasing hormone analogues produce slightly more consistent endometrial thinning than danazol, though both agents produce satisfactory results. The effect of these agents on longer-term post-operative outcomes such as amenorrhea and the need for further surgical intervention reduces with time. If progestogens are to be used at all it should only be within the context of a trial to formally evaluate them.

There is, therefore, a need for less expensive agents for endometrial thinning prior to endometrial ablation or other surgical procedures on the endometrial cavity and uterus.

Human endometrium is a unique tissue that undergoes sequential phases of proliferation, and secretory changes followed by tissue shedding and bleeding during menstruation. Proliferation of the endometrial cells occurs in response to estrogen stimulation particularly during the first half of the menstrual cycle (follicular or proliferative phase). Menstruation is the process by which the endometrium is discarded each month if pregnancy fails to occur. It involves sloughing of the endometrium over a period of days, bleeding and subsequent repair. Work carried out in the 1930s established that ovarian steroids, estrogen and progesterone, were responsible for the changes in endometrial structure and function throughout the cycle.

Within the uterus, the female sex steroids estrogen and progesterone play pivotal roles in endometrial development. More specifically, these steroids regulate a multitude of cellular processes, which include cell proliferation and differentiation, as well as regulation of vascular permeability, angiogenesis and adenogenesis. To bring about these changes, estrogen and progesterone must appropriately modulate a variety of factors, which include growth factors, cytokines, extracellular matrix proteins and adhesion molecules.

Steroids interact with their target organs via specific nuclear receptors. The expression of endometrial sex steroid receptors (progesterone receptor (PR), oestrogen receptor (ER), androgen receptor (AR), all of which are nuclear proteins, varies both temporally and spatially across the menstrual cycle. The expression of ER and PR are under dual control of estrogen and progesterone. Both endometrial ER and PR are up-regulated during the follicular phase by ovarian estrogen and subsequently down regulated in the luteal phase by progesterone acting at both the transcriptional and the post-transcriptional levels. Experiments with rhesus macaques that have been treated with oestrogen and progesterone indicate that the induction of menstruation is identical under the following two conditions: withdrawal of progesterone alone while estrogen is maintained, or withdrawal of both estrogen and progesterone. Furthermore, the administration of the antiprogestin, mifepristone (RU486) is associated with marked endometrial ECM breakdown and excessive menstrual bleeding.

Aromatase is a microsomal member of the cytochrome P450 hemoprotein-containing enzyme complex superfamily (P450arom, the product of the CYP19 gene) that catalyzes the rate-limiting step in the production of estrogens, that is, the conversion of androstenedione and testosterone via three hydroxylation steps to estrone and estradiol respectively. Aromatase activity is present in many tissues, such as the ovaries, the brain, adipose tissue, muscle, liver, breast tissue, and in malignant breast tumors. The main sources of circulating estrogens are the ovaries in premenopausal women and adipose tissue in postmenopausal women.

Aromatase is a good target for selective inhibition because estrogen production is a terminal step in the biosynthetic sequence. A large number of aromatase inhibitors have been developed and utilized in clinical studies over the last 20 years, mainly for treatment of breast cancer.

The first aromatase inhibitor to be used clinically was aminoglutethimide, which induces a medical adrenalectomy by inhibiting many other enzymes involved in steroid biosynthesis. Although aminoglutethimide is an effective hormonal agent in postmenopausal breast cancer, its use is complicated by the need for concurrent corticosteroid replacement. In addition side effects, like lethargy, rashes, nausea and fever, result in 8-15% of patients stopping the aminioglutethimide treatment. The lack of specificity and unfavorable toxicity profile of aminoglutethimide has led to a search for more specific aromatase inhibitors. In addition, the earlier aromatase inhibitors were not able to completely inhibit aromatase activity in premenopausal patients. Therefore, aromatase inhibitors have been primarily used for postmenopausal patients.

Aromatase inhibitors have been classified in a number of different ways, including first-, second-, and third-generation; steroidal and nonsteroidal; and by binding activity, i.e., reversible (ionic binding) and irreversible (suicide inhibitor, covalent binding). The most successful, third generation aromatase inhibitors are now available commercially for breast cancer treatment.

The commercially available agents include two nonsteroidal preparations, anastrozole and letrozole, and a steroidal agent, exemestane. Exemestane is available from Pfizer Inc., New York, N.Y. under the trademark Aromasin®; Anastrozole, is available from AstraZeneca under the trademark Arimidex® (ZN 1033); and letrozole is available from Novartis Pharmaceutical Corporation under the trademark Femara® CGS 20267). Anastrozole and letrozole are selective aromatase inhibitors, available for clinical use in North America, Europe and other parts of the world for treatment of postmenopausal breast cancer. These triazole (antifungal) derivatives are reversible, competitive aromatase inhibitors, which are highly potent and selective. Their intrinsic potency is considerably greater than that of aminoglutethimide, and at doses of 1-5 mg/day, they inhibit estrogen levels by 97% to >99%. This level of aromatase inhibition results in estradiol concentrations below detection by most sensitive immunoassays. The high affinity of aromatase inhibitors for aromatase is thought to reside in the –4 nitrogen of the triazole ring that coordinates with the heme iron atom of the aromatase enzyme complex. Aromatase inhibitors are completely absorbed after oral administration with mean terminal $t_{1/2}$ of approximately 45 hr (range, 30-60 hr). They are cleared from the systemic circulation mainly by the liver. Gastrointestinal disturbances account for most of the adverse events, although these have seldom limited therapy. Other adverse effects are asthenia, hot flashes, headache, and back pain.

The wide clinical safety of aromatase inhibitors, as well as the reduced cost of treatment, make these agents promising for use in treatment modalities for estrogen-dependant disorders, e.g., endometriosis and uterine fibroids. Although these agents are mainly used in postmenopausal women, most recently, we have reported the success of these agents in inhibiting estrogen production in women of the reproductive age group. Mitwally, et al., Aromatase Inhibition: A novel method of ovulation induction in women with polycystic ovarian syndrome, *Reprod. Technol.*, Vol. 10, No. 5, pages 244-247 (2000); Mitwally, et al., Use of an aromatase inhibitor for induction of ovulation in patients with an inadequate response to clomiphene citrate, *Fertil. Steril.*, Vol. 75, No. 2, 305-9 (2001); and Mitwally, et al., Aromatase inhibition improves ovarian response to FSH: A potential option for low responders during ovarian stimulation, *Fertil. Steril.*, Vol. 77, No. 4, pages 776-80 (2002).

Expression of the aromatase enzyme has been found in the endometrium in association with different estrogen disorders such as endometriosis and uterine fibroids. An "intracrine" effect of estrogen in these disorders has been suggested. Estrogen produced by local aromatase activity can exert its effects by readily binding to its nuclear receptor within the same cell. Disease-free endometrium and myometrium, on the other hand, lack aromatase expression. Therefore, we propose to use an aromatase inhibitor to cause thinning of the endometrium by decreasing estrogen production during the pre-operative period before endometrial ablation.

SUMMARY OF THE PRESENT INVENTION

In a method embodiment of the present invention, an aromatase inhibitor is administered to a patient during the pre-operative period before endometrial ablation in order to thin the endometrium by decreasing estrogen production. Reduction of estrogen production would reduce the proliferative capacity of the endometrial cells.

While not wishing to be bound by theory, we believe that such lowering of estrogen production would be achieved through a dual mechanism. First, by decreasing the circulating estrogen levels by inhibiting ovarian estrogen production, which is the main source of estrogen in women of the reproductive age, as well as inhibiting any contribution from extra ovarian tissue, such as fat and skin. Second, by decreasing estrogen production locally in the endometrium which comes from the local conversion of the circulating androgens into estrogen.

The practice of our invention involves the use of one or more of aromatase inhibitors, of the type described in detail hereinbelow, either alone or in combination with other aromatase inhibitors and/or other medications, including but not exclusive to other steroids or antisteroids, for endometrial preparation, mainly endometrial thinning before endometrial destruction with one or more of the methods of endometrial ablation, such as, but not restricted to, endometrial resection, endometrial ablation with electrocautery, e.g., roller ball, endometrial laser resection, as well as the new "second generation" endometrial ablation techniques, such as balloon thermal ablation, microwave endometrial ablation, endometrial thermal hydroablation, tubal cannulation, and the like.

The administration of the one or more aromatase inhibitors, alone or in combination with other medication(s) may be given as a single dose for one day or multiple days, or as multiple doses for one day or multiple days. Other medications may be started before, concomitant with, or after starting the aromatase inhibitor administration. Administration of the aromatase inhibitor(s) alone or in conjunction with other medications can start any time during the menstrual cycle, for any duration before the procedure of endometrial ablation The administration of the aromatase inhibitor(s) alone or in combination together, or in conjunction with other medications can be done orally, parenterally or through other known routes of pharmacologic administration of medications such as but not exclusive to transvaginally, transrectally, and through the skin or mucous membranes.

The present invention, supported by the above-mentioned scientific data including our own data on the success of the of aromatase inhibitors in suppressing estrogen levels in women in the reproductive age group (see, Mitwally, et al. articles, supra.), involves several hypotheses that can explain the success of aromatase inhibitors in altering the structure of the endometrium (mainly inducing endometrial thinning) by the following mechanisms:

The main hypothesis is the "endometrial thinning" hypothesis, i.e., preventing endometrial proliferation and disruption of the endometrium and its breakdown leading to endometrial thinning. Endometrial thinning is expected to improve the efficacy of any method of endometrial ablation in completely destroying the full thickness of the endometrium. This is clearly due to reducing the amount of tissue that needs to be destroyed to reach the subendometrial layer, thus preventing regeneration of the endometrium.

We propose that endometrial thinning by aromatase inhibition is the result of two mechanisms. The first is a direct mechanism involving "estrogen withdrawal" due to the rapid drop in estrogen levels due to inhibition of estrogen production by inhibiting the aromatase enzyme responsible for estrogen synthesis (both locally at the level of the endometrium and systemically in other tissues, mainly the ovaries). The second is an indirect mechanism, called herein "progesterone action deprivation" due to the suppression of progesterone receptors expression in the endometrium that is dependent on the presence of estrogen.

Both "estrogen withdrawal" and "progesterone action deprivation" are expected to produce a cascade of events, ultimately resulting in endometrial thinning by preventing endometrial proliferation and causing possible disruption of the endometrial integrity leading to its breakdown and further thinning. This thinning will occur irrespective of what stage of the menstrual cycle the aromatase inhibitor is given. Moreover, a short duration of treatment (i.e., a few days) before the endometrial ablation procedure will be enough to achieve optimum endometrial thinning that will enhance the outcome of endometrial ablation treatment.

A major advantage of the present invention over any of the currently available methods of endometrial preparation for endometrial ablation is its efficacy irrespective of the duration of treatment required, or the stage of the menstrual cycle, before endometrial ablation.

As indicated above, the currently available methods of endometrial preparation before endometrial ablation have major drawbacks, such as high cost, as well as requiring long periods of treatment (i.e., several weeks) before endometrial preparation can effectively be achieved.

To summarize, the advantages of the present invention over the currently available methods for endometrial preparation before endometrial ablation:

(1) shorter duration of application before endometrial destruction procedure (about three to 12 times shorter);

(2) efficacy when administered at any stage of the menstrual cycle;

(3) lower treatment cost than currently available agents (about three to 10 times less);

(4) more convenient regimen: single daily oral administration for a short period of time (about one week);

(5) high safety profile including high tolerability and absence of significant interaction with other medications or serious adverse effects; and (6) higher success rates in enhancing the treatment outcome of endometrial destruction defined as:

(7) more favorable procedure parameters, i.e., less operative time, more ease of surgery and less intra/post-operative complications; and (8) a favorable rate of postoperative amenorrhea.

In one embodiment of the invention, an aromatase inhibitor is administered in one or more daily doses, either alone or in combination with, a plurality of daily doses of other pharmaceutical agents, including hormones.

The invention also provides for the use of one or more daily doses of at least one aromatase inhibitor in amounts effective to reduce serum estrogen levels for endometrial preparation, mainly endometrial thinning, before endometrial ablation.

While a single aromatase inhibitor is preferred for use in the present invention, combinations of aromatase inhibitors may be used especially a combination of aromatase inhibitors having different half-lives. The aromatase inhibitor is preferably selected from aromatase inhibitors having a half-life of about 8 hours to about 4 days, more preferably from aromatase inhibitors having a half-life of about 2 days. Most beneficial are those aromatase inhibitors selected from non-steroidal and reversible aromatase inhibitors. More detail on the types of aromatase inhibitors that may be used in the methods, uses and preparations of the present invention appears subsequently herein.

The aromatase inhibitors that have been found to be most useful of the commercially available forms are those in oral form. This form offers clear advantages over other forms, including convenience and patient compliance. Preferred aromatase inhibitors of those that are commercially available include anastrozole, letrozole, vorozole and exemestane. Exemestane (Aromasin™) is an example of a steroidal aromatase inhibitor that may be used in the present invention.

The daily doses required for the present invention depend on the type of aromatase inhibitor that is used. Some inhibitors are more active than others and hence lower amounts of the former inhibitors could be used.

Examples of preferred suitable dosages are as follows. When the aromatase inhibitor is letrozole, it is preferably administered in a daily dose of from about 2.5 mg to about 50.0 mg. When the aromatase inhibitor is anastrozole, preferably, it is administered in a daily dose of from about 1 mg to about 20 mg. When the aromatase inhibitor is vorozole, the preferred daily dose is from about 4 to about 40 mg. Exemestane is preferably administered in a daily dose of about 25 to 250 mg. Preferred are 1 to 10 daily doses of the aromatase inhibitor with administration for 1-30 days before endometrial ablation. Most preferably the daily doses of the aromatase inhibitor comprise about 10 daily doses.

In addition to the foregoing, it is important to stress the fact that the success of aromatase inhibitors in endometrial preparation, mainly endometrial thinning before endometrial ablation can be extended to other related indications that require endometrial preparation. This includes, but is not limited to, endometrial preparation, mainly endometrial thinning before various procedures on the endometrial cavity and uterus, such as hysteroscopic procedures, both diagnostic and therapeutic, transcervical sterilization, etc.

Aromatase inhibitors have not been used in women of the reproductive age group until recently. We found that estrogen levels following induction or augmentation of ovulation with aromatase inhibitors were significantly lower (especially serum E2 concentration/mature follicle) when compared with conventional stimulation protocols.

Thus, the present invention provides a method for endometrial preparation, mainly endometrial thinning before endometrial ablation to enhance the treatment outcome, as well as other related procedures on the endometrial cavity and the uterus.

As used herein, the term "aromatase inhibitors" is to be understood to include substances that inhibit the enzyme aromatase (=estrogen synthetase), which is responsible for converting androgens to oestrogens.

Aromatase inhibitors may have a non-steroidal or a steroidal chemical structure. According to the present invention, both non-steroidal aromatase inhibitors and steroidal aromatase inhibitors can be used.

Aromatase inhibitors is to be understood to include especially those substances that in a determination of the in vitro inhibition of aromatase activity exhibit $IC_{50}$ values of $10^{-5}$ M or lower, especially $10^{-6}$ M or lower, preferably $10^{-7}$ M or lower and most especially $10^{-8}$ M or lower.

The in vitro inhibition of aromatase activity can be demonstrated, for example, using the methods described in *J. Biol. Chem.*, Vol. 249, page 5364 (1974) or in *J. Enzyme Inhib.*, Vol. 4, page 169 (1990). In addition, $IC_{50}$ values for aromatase inhibition can be obtained, for example, in vitro by a direct product isolation method relating to inhibition of the conversion of 4-$^{14}$ C-androstenedione to 4-$^{14}$ C-oestrone in human placental microsomes.

Aromatase inhibitors are to be understood to include most especially substances for which the minimum effective dose, in the case of in vivo aromatase inhibition, is 10 mg/kg or less, especially 1 mg/kg or less, preferably 0.1 mg/kg or less and most preferably 0.01 mg/kg or less.

In vivo aromatase inhibition can be determined, for example, by the following method described in *J. Enzyme Inhib.*, Vol. 4, page 179 (1990):

Androstenedione (30 mg/kg subcutaneously) is administered on its own or together with an aromatase inhibitor (orally or subcutaneously) to sexually immature female rats for a period of 4 days. After the fourth administration, the rats are sacrificed and the uteri are isolated and weighed. The aromatase inhibition is determined by the extent to which the hypertrophy of the uterus induced by the administration of androstenedione alone is suppressed or reduced by the simultaneous administration of the aromatase inhibitor.

The following groups of compounds are listed as examples of aromatase inhibitors useful in the practice of the invention. Each individual group forms a group of aromatase inhibitors that can be used successfully in accordance with the present invention:

(a) The compounds of formulae I and I* as defined in European Patent Publication No. EP-A-165 904. These are especially the compounds of Formula I

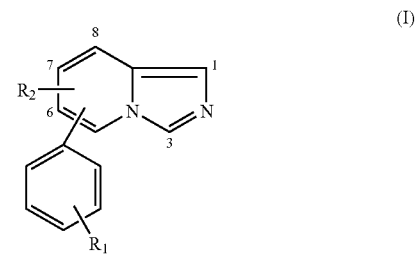

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, -thiomorpholino, N-piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2$-$C_7$ alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and the compounds of Formula I*

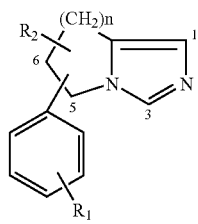

(I*)

wherein n is 0, 1, 2, 3 or 4; and $R_1$ and $R_2$ are as defined above for Formula I; it being possible for the phenyl ring in the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or by halogen; it being possible in a compound of Formula I* for the two substituents $C_6H_4$—$R_1$ and $R_2$ to be linked to each of the saturated carbon atoms of the saturated ring, either both to the same carbon atom or both to different carbon atoms, and pharmaceutically acceptable salts thereof.

Individual compounds that may be given special mention here are:

(1) 5-(p-cyanophenyl)imidazo[1,5-a]pyridine,
(2) 5-(p-ethoxycarbonylphenyl)imidazo[1,5-a]pyridine,
(3) 5-(p-carboxyphenyl)imidazo[1,5-a]pyridine,
(4) 5-(p-tert-butylaminocarbonylphenyl)imidazo[1,5-a]pyridine,
(5) 5-(p-ethoxycarbonylphenyl)-5,6,7,8-tetrahydroimidazo[1,5-a]pyridine,
(6) 5-(p-carboxyphenyl)-5,6,7,8-tetrahydroimidazo[1,5-a]pyridine,
(7) 5-(p-carbamoylphenyl)-5,6,7,8-tetrahydroimidazo[1,5-a]pyridine,
(8) 5-(p-tolyl)-5,6,7,8-tetrahydroimidazo[1,5-a]pyridine,
(9) 5-(p-hydroxymethylphenyl)imidazo[1,5-a]pyridine,
(10) 5-(p-cyanophenyl)-7,8-dihydroimidazo[1,5-a]pyridine,
(11) 5-(p-bromophenyl)-5,6,7,8-tetrahydroimidazo[1,5-a]pyridine,
(12) 5-(p-hydroxymethylphenyl)-5,6,7,8-tetrahydroimidazo[1,5-a]pyridine,
(13) 5-(p-formylphenyl)-5,6,7,8-tetrahydroimidazo[1,5-a]pyridine,
(14) 5-(p-cyanophenyl)-5-methylthio-5,6,7,8-tetrahydroimidazo[1,5-a]pyridine,
(15) 5-(p-cyanophenyl)-5-ethoxycarbonyl-5,6,7,8-tetrahydroimidazo[1,5-a]pyridine,
(16) 5-(p-aminophenyl)-5,6,7,8-tetrahydroimidazo[1,5-a]pyridine,
(17) 5-(p-formylphenyl)imidazo[1,5-a]pyridine,
(18) 5-(p-carbamoylphenyl)imidazo[1,5-a]pyridine,
(19) 5H-5-(4-tert-butylaminocarbonylphenyl)-6,7-dihydropyrrolo[1,2-c]imidazole,
(20) 5H-5-(4-cyanophenyl)-6,7-dihydropyrrolo[1,2-c]imidazole,
(21) 5H-5-(4-cyanophenyl)-6,7,8,9-tetrahydroimidazo[1,5-a]azepine,
(22) 5-(4-cyanophenyl)-6-ethoxycarbonylmethyl-5,6,7,8-tetrahydroimidazo[1,5-a]pyridine,
(23) 5-(4-cyanophenyl)-6-carboxymethyl-5,6,7,8-tetrahydroimidazo[1,5-a]pyridine
(24) 5-benzyl-5-(4-cyanophenyl)-5,6,7,8-tetrahydroimidazo[1,5-a]pyridine,
(25) 7-(p-cyanophenyl)-5,6,7,8-tetrahydroimidazo[1,5-a]pyridine,
(26) 7-(p-carbamoylphenyl)-5,6,7,8-tetrahydroimidazo[1,5-a]pyridine,
(27) 5-(p-cyanophenyl)-5,6,7,8-tetrahydroimidazo[1,5-a]pyridine(=Fadrozol).

(b) The compounds of Formula I as defined in European Patent Publication No. EP-A 236 940. These are especially the compounds of Formula I

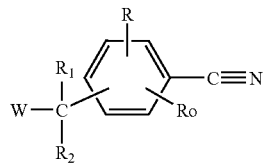

(I)

wherein R and $R_0$, independently of one another, are each hydrogen or lower alkyl, or R and $R_0$ at adjacent carbon atoms, together with the benzene ring to which they are bonded, form a naphthalene or tetrahydronaphthalene ring; wherein $R_1$ is hydrogen, lower alkyl, aryl, aryl-lower alkyl or lower alkenyl; $R_2$ is hydrogen, lower alkyl, aryl, aryl-lower alkyl, (lower alkyl, aryl or aryl-lower alkyl)-thio or lower alkenyl, or wherein $R_1$ and $R_2$ together are lower alkylidene or $C_4$-$C_6$ alkylene; wherein W is 1-imidazolyl, 1-(1,2,4 or 1,3,4)-triazolyl, 3-pyridyl or one of the mentioned heterocyclic radicals substituted by lower alkyl; and aryl within the context of the above definitions has the following meanings: phenyl that is unsubstituted or substituted by one or two substituents from the group lower alkyl, lower alkoxy, hydroxy, lower alkanoyloxy, nitro, amino, halogen, trifluoromethyl, cyano, carboxy, lower alkoxycarbonyl, carbamoyl, -lower alkylcarbamoyl, N,N-di-lower alkylcarbamoyl, lower alkanoyl, benzoyl, lower alkylsulfonyl, sulfamoyl, -lower alkylsulfamoyl and N,N-di-lower alkylsulfamoyl; also thienyl, indolyl, pyridyl or furyl, or one of the four last-mentioned heterocyclic radicals monosubstituted by lower alkyl, lower alkoxy, cyano or by halogen; and pharmaceutically acceptable salts thereof.

Individual compounds from that group that may be given special mention are:

(1) 4-[alpha-(4-cyanophenyl)-1-imidazolylmethyl]-benzonitrile,
(2) 4-[alpha-(3-pyridyl)-1-imidazolylmethyl]-benzonitrile,
(3) 4-[alpha-(4-cyanobenzyl)-1-imidazolylmethyl]-benzonitrile,
(4) 1-(4-cyanophenyl)-1-(1-imidazolyl)-ethylene,
(5) 4-[alpha-(4-cyanophenyl)-1-(1,2,4-triazolyl)methyl]-benzonitrile,
(6) 4-[alpha-(4-cyanophenyl)-3-pyridylmethyl]-benzonitrile.

(c) The compounds of Formula I as defined in European Patent Publication No. EP-A-408 509. These are especially the compounds of Formula I

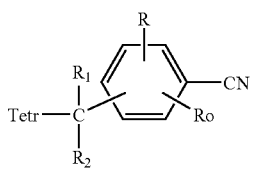

(I)

wherein Tetr is 1- or 2-tetrazolyl that is unsubstituted or substituted in the 5-position by lower alkyl, phenyl-lower alkyl or by lower alkanoyl; R and $R_2$, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$-$C_6$ cycloalkyl, $C_3$-$C_6$ cycloalkyl-lower alkyl, lower alkylthio, arylthio or aryl-lower alkylthio; or $R_1$ and $R_2$ together are straight-chained $C_4$-$C_6$ alkylene that is unsubstituted or substituted by lower alkyl, or are a group —$(CH_2)_m$-1,2-phenylene-$(CH_2)_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below; aryl in the above definitions being phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; heteroaryl in the above definitions being an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above; and pharmaceutically acceptable salts thereof.

Individual compounds from that group that may be given special mention are:
(1) 4-(2-tetrazolyl)methyl-benzonitrile,
(2) 4-[a-(4-cyanophenyl)-(2-tetrazolyl)methyl]-benzonitrile,
(3) 1-cyano-4-(1-tetrazolyl)methyl-naphthalene,
(4) 4-[a-(4-cyanophenyl)-(1-tetrazolyl)methyl]-benzonitrile.

(d) The compounds of Formula I as defined in European Patent Application No. 91810110.6. These are especially the compounds of Formula I

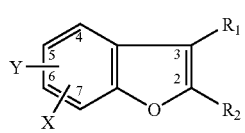

wherein X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen and/or by trifluoromethyl; Y is a group —$CH_2$-A wherein A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl, or Y is hydrogen, $R_1$ and $R_1$, independently of one another, are each hydrogen, lower alkyl or a group —$CH_2$-A as defined for Y, or $R_1$ and $R_2$ together are —$(CH_2)_n$— wherein n is 3, 4 or 5, with the proviso that one of the radicals Y, $R_1$ and $R_2$ is a group —$CH_2$-A, with the further proviso that in a group —$CH_2$-A as a meaning of $R_1$ or $R_2$, A is other than 1-imidazolyl when X is bromine, cyano or carbamoyl, and with the proviso that in a group —$CH_2$-A as a meaning of Y, A is other than 1-imidazolyl when X is halogen or lower alkoxy, $R_1$ is hydrogen and $R_2$ is hydrogen or lower alkyl, and pharmaceutically acceptable salts thereof.

Individual compounds from that group that may be given special mention are:
(1) 7-cyano-4-[1-(1,2,4-triazolyl)methyl]-2,3-dimethylbenzofuran,
(2) 7-cyano-4-(1-imidazolylmethyl)-2,3-dimethylbenzofuran,
(3) 7-carbamoyl-4-(1-imidazolylmethyl)-2,3-dimethylbenzofuran,
(4) 7-N-(cyclohexylmethyl)carbamoyl-4-(1-imidazolylmethyl)-2,3-dimethylbenzofuran.

(e) The compounds of Formula I as defined in Swiss Patent Application No. 1339/90-7. These are especially the compounds of Formula I

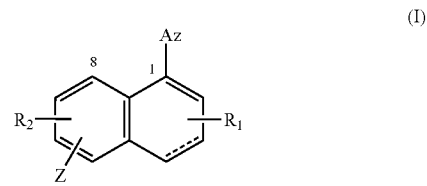

wherein the dotted line denotes an additional bond or no additional bond, Az is imidazolyl, triazolyl or tetrazolyl bonded via a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and $R_1$ and $R_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and pharmaceutically acceptable salts thereof.

Individual compounds from that group that may be given special mention are:
(1) 6-cyano-1-(1-imidazolyl)-3,4-dihydronaphthalene,
(2) 6-cyano-1-[1-(1,2,4-triazolyl)]-3,4-dihydronaphthalene,
(3) 6-chloro-1-(1-imidazolyl)-3,4-dihydronaphthalene,
(4) 6-bromo-1-(1-imidazolyl)-3,4-dihydronaphthalene.

(f) The compounds of Formula I as defined in Swiss Patent Application No. 3014/90-0. These are especially the compounds of Formula I

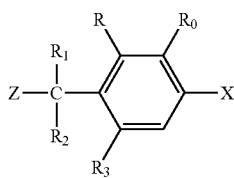

(I)

wherein Z is a five-membered nitrogen-containing heteroaromatic ting selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$— wherein the single bone is linked to the benzene ring; X is cyano; and X may also be halogen when $R_2$ and $R_3$ together are —$(CH_2)_3$— or $R_1$ and $R_1$ and $R_3$ together are a group =CH—$(CH_2)_2$—; and pharmaceutically acceptable salts thereof.

Individual compounds from that group that may be given special mention are:
(1) 4-[a-(4-cyanophenyl)-a-hydroxy-5-isothiazolylmethyl]-benzonitrile.
(2) 4-[a-(4-cyanophenyl)-5-isothiazolylmethyl]-benzonitrile,
(3) 4-[a-(4-cyanophenyl)-5-thiazolylmethyl]-benzonitrile,
(4) 1-(4-cyanophenyl)-1-(5-thiazolyl)-ethylene,
(5) 6-cyano-1-(5-isothiazolyl)-3,4-dihydronaphthalene,
(6) 6-cyano-1-(5-thiazolyl)-3,4-dihydronaphthalene.

(g) The compounds of formula VI as defined in Swiss Patent Application No. 3014/90-0.
These are especially the compounds of formula VI

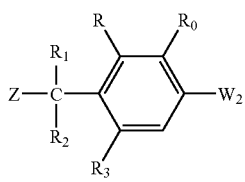

(VI)

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl). 5-(1,2,3-oxadiazolyl) 3-(1,2,5-thiadiazolyl), 3-(1,2,5-oxadiazolyl), 4-isothiazolyl. 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are each hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene, and $W_2$ is halogen, hydroxy, lower alkoxy, aryl-lower alkoxy or aryloxy; aryl in each case being phenyl that is unsubstituted or substituted by lower alkyl, lower alkoxy, hydroxy, halogen or by trifluoromethyl; and pharmaceutically acceptable salts thereof.

Individual compounds from that group that may be given special mention are:
(1) bis(4,4'-bromophenyl)-(5-isothiazolyl)methanol,
(2) bis(4,4'-bromophenyl)-(5-isothiazolyl)methane,
(3) bis(4,4'-bromophenyl)-(5-thiazolyl)methanol,
(4) bis(4,4'-bromophenyl)-(5-thiazolyl)methane, (h) The compounds of Formula I as defined in Swiss Patent Application No. 3923/90-4. These are especially the compounds of Formula I

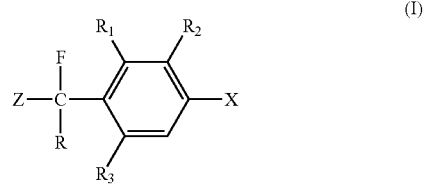

(I)

wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl, triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl: $R_1$ and $R_2$, independently of one another, are each hydrogen or lower alkyl; or $R_1$ and $R_2$ together are $C_3$-$C_4$ alkylene, or a benzo group that is unsubstituted or substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, -hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoindolyl, benzimidazolyl, benzopyrazolyl or benzotriazolyl; wherein aryl is phenyl or naphthyl, these radicals being unsubstituted or substituted by from 1 to 4 substituents from the group consisting of lower alkyl, lower alkenyl, lower alkynyl, lower alkylene (linked to two adjacent carbon atoms), $C_3$-$C_8$ cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$-$C_8$ cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"— (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, -cycloalkyl-lower alkylcarbamoyl, N-(lower alkyl-substituted cycloalkyl)-lower alkylcarbamoyl, N-hydroxycarbamoyl, N-phenyl-lower alkylcarbamoyl, -phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen and/or by trifluoromethyl; wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl; and pharmaceutically acceptable salts thereof.

Those compounds are especially the compounds of Formula I whereto Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidyl, 5-pyrimidinyl or 2-pyrazinyl; $R_1$ and $R_2$, independently of one another, are each hydrogen or lower alkyl; or $R_1$ and $R_2$ together are 1,4-butylene or a benzo group; R is lower alkyl; phenyl that is unsubstituted or substituted by cyano, carbamoyl, halogen, lower alkyl, trifluoromethyl, hydroxy, lower alkoxy or by phenoxy; or benzotriazolyl or benzo[b]furanyl, the last two radicals being unsubstituted or substituted by from 1 to 3 identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl 2-tetrazolyl; and pharmaceutically acceptable salts thereof.

Individual compounds that may be given special mention here are:
(1) 4-[a-4-cyanophenyl)-a-fluoro-1-(1,2,4-triazolyl)methyl]-benzonitrile,
(2) 4-[a-(4-cyanophenyl)-a-fluoro-(2-tetrazolyl)methyl]-benzonitrile,
(3) 4-[a-(4-cyanophenyl)-a-fluoro-(1-tetrazolyl)methyl]-benzonitrile,
(4) 4-[a-(4-cyanophenyl)-a-fluoro-(1-imidazolyl)methyl]-benzonitrile,
(5) 1-methyl-6-[a-(4-chlorophenyl)-a-fluoro-1-(1,2,4-triazolyl)methyl]-benzotriazole,
(6) 4-[a-(4-cyanophenyl)-a-fluoro-1-(1,2,3-triazolyl)methyl]-benzo nitrile,
(7) 7-cyano-4-[a-(4-cyanophenyl)-a-fluoro-1-(1,2,4-triazolyl)methyl]-2,3-dimethylbenzo[b]furan,
(8) 4-[a-(4-bromophenyl)-a-fluoro-1-(1,2,4-triazolyl)methyl]-benzo nitrile,
(9) 4-[a-(4-cyanophenyl)-a-fluoro-(5-pyrimidyl)methyl]-benzonitrile,
(10) 4-[a-(4-bromophenyl)-a-fluoro-(5-pyrimidyl)methyl]-benzonitrile,
(11) 4-[a-(4-cyanophenyl)-a-fluoro-(3-pyridyl)methyl]-benzonitrile,
(12) 7-bromo-4-[a-(4-cyanophenyl)-a-fluoro-(1-imidazolyl)methyl]-2,3-dimethylbenzo[b]furan,
(13) 7-bromo-4-[a-(4-cyanophenyl)-a-fluoro-1-(1,2,4-triazolyl)methyl]-2,3-dimethylbenzo[b]furan,
(14) 4-[a-(4-cyanophenyl)-a-fluoro-(5-pyrimidyl)methyl]-benzonitrile,
(15) 4-[a-(4-bromophenyl)-a-fluoro-(5-pyrimidyl)methyl]-benzonitrile,
(16) 4-[a-(4-cyanophenyl)-1-(1,2,3-triazolyl)methyl]-benzonitrile,
(17) 2,3-dimethyl-4-[a-(4-cyanophenyl)-1-(1,2,4-triazolyl)methyl]-7-cyano-benzo[b]furan,
(18) 4-[a-(4-cyanophenyl)-(5-pyrimidyl)methyl]-benzonitrile,
(19) 4-[a-(4-bromophenyl)-(5-pyrimidyl)methyl]-benzonitrile,
(20) 2,3-dimethyl-4-[a-(4-cyanophenyl)-(1-imidazolyl)methyl]-7-bromo-benzo[b]furan,
(21) 2,3-dimethyl-4-[a-(4-cyanophenyl)-1-(1,2,4-triazolyl)methyl]-7-bromo-benzo-[b]furan.

(I) The compounds of Formula I as defined in European Patent Publication No. EP-A-114 033. These are especially the compounds of Formula I

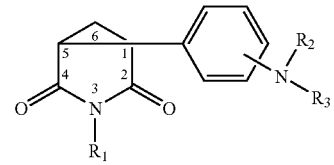

wherein $R_1$ is hydrogen, $R_2$ is hydrogen, sulfo, $C_1$-$C_7$ alkanoyl or $C_1$-$C_7$ alkanesulfonyl and $R_3$ is hydrogen, or wherein $R_1$ is $C_1$-$C_{12}$ alkyl, $C_{·2}$-$C_{12}$ alkenyl, $C_2$-$C_7$ alkynyl, $C_3$-$C_{10}$ cycloalkyl, $C_3$-$C_{·10}$ cycloalkenyl, $C_{·3}$3-$C_6$ cycloalkyl-$C_1$-$C_4$ alkyl, $C_3$-$C_6$ cycloalkyl-$C_{·2}$-$C_4$ alkenyl or $C_3$-$C_6$ cycloalkenyl-$C_1$-$C_4$ alkyl, $R_2$ is hydrogen, $C_1$-$C_7$ alkyl, sulfo, $C_1$-$C_7$ alkanoyl or $C_1$-$C_7$ alkanesulfonyl and $R_3$ is hydrogen or $C_1$-$C_7$ alkyl, and salts of those compounds.

Individual compounds from that group that may be given special mention are:
(1) 1-(4-aminophenyl)-3-methyl-3-azabicyclo[3.1.0]hexane-2,4-dione,
(2) 1-(4-aminophenyl)-3-n-propyl-3-azabicyclo[3.1.0]hexane-2,4-dione,
(3) 1-(4-aminophenyl)-3-isobutyl-3-azabicyclo[3.1.0]hexane-2,4-dione,
(4) 1-(4-aminophenyl)-3-n-heptyl-3-azabicyclo[3.1.0]hexane-2,4-dione,
(5) 1-(4-aminophenyl)-3-cyclohexylmethyl-3-azabicyclo[3.1.0]hexane-2,4-dione.

(j) The compounds of Formula I as defined in European Patent Publication No. EP-A-166 692. These are especially the compounds of Formula I

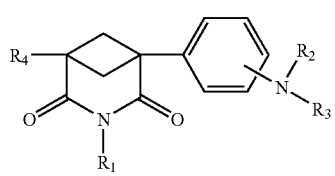
(I)

wherein $R_1$ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino amino or by halogen, $R_2$ is hydrogen, lower alkyl, sulfo, lower alkanoyl or lower alkanesulfonyl, sulfonyl, $R_3$ is hydrogen or lower alkyl and $R_4$ is hydrogen, lower alkyl, phenyl or phenyl substituted by —N($R_2$)($R_3$), and salts thereof, radicals described as "lower" containing up to and including 7 carbon atoms.

Individual compounds from that group that may be given special mention are:
(1) 1-(4-aminophenyl)-3-n-propyl-3-azabicyclo[3.1.1]heptane-2,4-dione,
(2) 1-(4-aminophenyl)-3-methyl-3-azabicyclo[3.1.1]heptane-2,4-dione,
(3) 1-(4-aminophenyl)-3-n-decyl-3-azabicyclo[3.1.1]heptane-2,4-dione,
(4) 1-(4-aminophenyl)-3-cyclohexyl-3-azabicyclo[3.1.1]heptane-2,4-dione,
(5) 1-(4-aminophenyl)-3-cyclohexylmethyl-3-azabicyclo[3.1.1]heptane-2,4-dione.

(k) The compounds of Formula I as defined in European Patent Publication No. EP-A-356 673. These are especially the compounds of Formula I

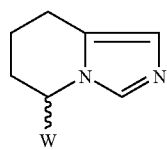
(I)

wherein W (a) is a 2-naphthyl or 1-anthryl radical, wherein each benzene ring is unsubstituted or substituted by a substituent selected from halogen, hydroxy, carboxy, cyano and nitro; or (.beta.) is 4-pyridyl, 2-pyrimidyl or 2-pyrazinyl, each of those radicals being unsubstituted or substituted by a substituent selected from halogen, cyano, nitro, $C_1$-$C_4$ alkoxy and $C_2$-$C_5$ alkoxycarbonyl; and pharmaceutically acceptable salts thereof.

Individual compounds from that group that may be given special mention are:
(1) 5-(2'-naphthyl)-5,6,7,8-tetrahydroimidazo[1,5-a]pyridine,
(2) 5-(4'-pyridyl)-5,6,7,8-tetrahydroimidazo[1,5-a]pyridine.

(l) The compounds of Formula I or Ia as defined in European Patent Publication No. EP-A-337 929. These are especially the compounds of Formula I/Ia

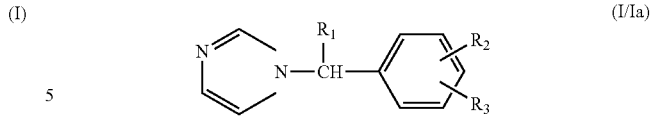
(I/Ia)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is benzyloxy, 3-bromo-, 4-bromo-, 4-chloro-, 2,3-, 2,4-, 4,5- or 4,6-dichloro-benzyloxy, and $R_3$ is cyano; $C_2$-$C_{10}$ alkanoyl that is unsubstituted or mono- or poly-substituted by halogen, methoxy, amino, hydroxy and/or by cyano; benzoyl that is unsubstituted or substituted by one or more substituents from the group halogen, $C_1$-$C_4$ alkyl, methoxy, amino, hydroxy and cyano; carboxy, (methoxy, ethoxy or butoxy)-carbonyl, carbamoyl, N-isopropylcarbamoyl, N-phenylcarbamoyl, N-pyrrolidylcarbamoyl, nitro or amino; and salts thereof.

Individual compounds from that group that may be given special mention are:
(1) 4-(2,4-dichlorobenzyloxy)-3-[1-(1-imidazolyl)-butyl]-benzonitrile,
(2) (4-(4-bromobenzyloxy)-3-[1-(1-imidazolyl)-butyl]-phenyl pentyl ketone,
(3) 4-(4-bromobenzyloxy)-3-[1-(1-imidazolyl)-butyl]-benzanilide,
(4) 4-(4-bromobenzyloxy)-3-[1-(1-imidazolyl)-butyl]-benzoic acid,
(5) 3-(2,4-dichlorobenzyloxy)-4-[1-(1-imidazolyl)-butyl]-benzonitrile,
(6) 3-(2,4-dichlorobenzyloxy)-4-[1-(1-imidazolyl)-butyl]-benzoic acid methyl ester,
(7) 3-(2,4-dichlorobenzyloxy)-4-[1-(1-imidazolyl)-butyl]-benzoic acid,
(8) 3-(3-bromobenzyloxy)-4-[1-(1-imidazolyl)-butyl]-benzonitrile,
(9) 4-(3-bromobenzyloxy)-3-[1-(1-imidazolyl)-butyl]-benzonitrile,
(10) 3-(4-bromobenzyloxy)-4-[1-(1-imidazolyl)-butyl]-benzoic acid,
(11) 3-(4-bromobenzyloxy)-4-[1-(1-imidazolyl)-butyl]-benzanilide,
(12) 3-(4-bromobenzyloxy)-4-[1-(1-imidazolyl)-butyl]-phenyl pentyl ketone,
(13) 4-(4-bromobenzyloxy)-3-[1-(1-imidazolyl)-butyl]-benzonitrile,
(14) 3-(4-bromobenzyloxy)-4-[1-(1-imidazolyl)-butyl]-benzonitrile,
(15) 4-nitro-2-[1-(1-imidazolyl)-butyl]-phenyl-(2,4-dichlorobenzyl)ether,
(16) 4-amino-2-[1-(1-imidazolyl)-butyl]-phenyl-(2,4-dichlorobenzyl)ether,
(17) (2,4-dichlorobenzyl)-[2-(1-imidazolyl-methyl)-4-nitrophenyl]ether.

(m) The compounds of Formula I as defined in European Patent Publication No. EP-A-337 928. These are especially the compounds of Formula I

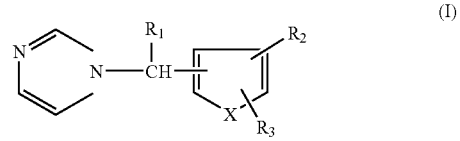
(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, -isopropylcarbamoyl, N-phenylcarbamoyl, N-pyrrolidylcarbonyl; $C_2$-$C_{10}$ alkanoyl that is unsubstituted or mono- or poly-substituted by halogen, methoxy, ethoxy, amino, hydroxy and/or by cyano; or benzoyl that is unsubstituted or substituted by one or more substituents from the group halogen, $C_1$-$C_4$ alkyl, methoxy, ethoxy, amino, hydroxy and cyano, $R_3$ is hydrogen, benzyloxy, 3-bromo-, 4-bromo-, 4-chloro-, 2,3-, 2,4-, 4,5- or 4,6-dichlorobenzyloxy, and X is —CH═; —CH═N(—O)— or —S—; and salts thereof.

Individual compounds from that group that may be given special mention are:
(1) 5-[1-(1-imidazolyl)-butyl]-thiophene-2-carbonitrile,
(2) 2-[1-(1-imidazolyl)-butyl]-thiophene-4-carbonitrile,
(3) 2-[1-(1-imidazolyl)-butyl]-4-bromo-thiophene,
(4) 2-[1-(1-imidazolyl)-butyl]-5-bromo-thiophene,
(5) 5-[1-(1-imidazolyl)-butyl]-2-thienyl pentyl ketone,
(6) 5-[1-(1-imidazolyl)-butyl]-2-thienyl ethyl ketone,
(7) 5-(4-chlorobenzyloxy)-4-[1-(1-imidazolyl)-pentyl]-pyridine-2-carbonitrile,
(8) 3-(4-chlorobenzyloxy)-4-[1-(1-imidazolyl)-pentyl]-pyridine-2-carbonitrile,
(9) 3-(4-chlorobenzyloxy)-4-[1-(1-imidazolyl)-pentyl]-pyridine-N-oxide,
(10) 3-(4-chlorobenzyloxy)-4-[1-(1-imidazolyl)-pentyl]-pyridine.

(n) The compounds of Formula I as defined in European Patent Publication No. EP-A-340 153. These are especially the compounds of Formula I

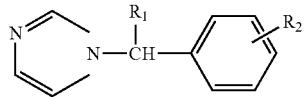

(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, and $R_2$ is a radical from the group methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; or $R_2$ is formyl or derivatised formyl that can be obtained by reaction of the formyl group with an amine or amine derivative from the group hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents from the group halogen, $C_1$-$C_4$-alkyl, methoxy, amino, hydroxy and cyano; carboxy, (methoxy, ethoxy or butoxy)carbonyl, carbamoyl, N-isopropylcarbamoyl, N-phenylcarbamoyl or N-pyrrolidylcarbonyl; and salts thereof.

Individual compounds from that group that may be given special mention are:
(1) 4-(1-(1-imidazolyl)-butyl)-benzoic acid methyl ester,
(2) 4-(1-(1-imidazolyl)-butyl)-benzoic acid butyl ester,
(3) 4-(1-(1-imidazolyl)-butyl)-phenyl-acetonitrile,
(4) 4-(1-(1-imidazolyl)-butyl)-benzaldehyde,
(5) 4-(1-(1-imidazolyl)-butyl)-benzyl alcohol,
(6) {4-[1-(1-imidazolyl)-butyl]-phenyl}-2-propyl ketone,
(7) 4-[1-(1-imidazolyl)-butyl]-phenyl propyl ketone,
(8) 4-[1-(1-imidazolyl)-butyl]-phenyl butyl ketone,
(9) 4-[1-(1-imidazolyl)-butyl]-phenyl pentyl ketone,
(10) 4-[1-(1-imidazolyl)-butyl]-phenyl hexyl ketone.

(o) The compounds of Formula I as defined in German Patent Application No. DE-A-4 014 006. These are especially the compounds of Formula I

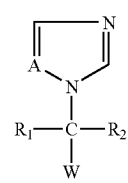

(I)

wherein A is an N-atom or a CH radical and W is a radical of the formula

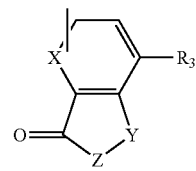

wherein X is an oxygen or a sulfur atom or a —CH═CH— group and Y is a methylene group, an oxygen or a sulfur atom and Z is a —(CH$_2$)$_n$— group wherein n=1, 2 or 3 and either
a) $R_3$ in W is a hydrogen atom and $R_1$ and $R_2$, independently of one another, are each a hydrogen atom, a $C_1$- to $C_{10}$ alkyl group or a $C_3$- to $C_7$ cycloalkyl group, or
b) $R_2$ is as defined under a) and $R_1$ together with $R_3$ forms a —(CH$_2$)$_m$— group wherein m=2, 3, or 4, and their pharmaceutically acceptable addition salts with acids.

Individual compounds from that group that may be given special mention are:
(1) 5-[1-(1-imidazolyl)-butyl]-1-indanone,
(2) 7-[1-(1-imidazolyl)-butyl]-1-indanone,
(3) 6-[1-(1-imidazolyl)-butyl]-1-indanone,
(4) 6-(1-imidazolyl)-6,7,8,9-tetrahydro-1H-benz[e]inden-3(2H)-one,
(5) 2-[1-(1-imidazolyl)-butyl]-4,5-dihydro-6-oxo-cyclopenta[b]-thiophene,
(6) 6-[1-(1-imidazolyl)-butyl]-3,4-dihydro-2H-naphthalen-1-one,
(7) 2-[1-(1-imidazolyl)-butyl]-6,7-dihydro-5H-benzo[b]thiophen-4-one,
(8) 6-[1-(1-imidazolyl)-butyl]-2H-benzo[b]furan-3-one,
(9) 5-[cyclohexyl-(1-imidazolyl)-methyl]-1-indanone,
(10) 2-[1-(1-imidazolyl)-butyl]-4,5-dihydro-6H-benzo[b]thiophen-7-one,
(11) 5-[1-(1-imidazolyl)-1-propyl-butyl]-1-indanone,
(12) 2-[1-(1-imidazolyl)-butyl]-4,5-dihydro-6H-benzo[b]thiophen-7-one,
(13) 2-[1-(1-imidazolyl)-butyl]-4,5-dihydro-6-oxo-cyclopenta[b]-thiophene,
(14) 5-(1-imidazolylmethyl)-1-indanone,
(15) 5-[1-(1,2,4-triazolyl)-methyl]-1-indanone.

(p) The compounds of Formula I as disclosed in German Patent Application No. DE-A-3 926 365. These are especially the compounds of Formula I

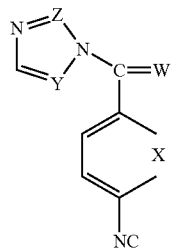

(I)

wherein W' is a cyclopentylidene, cyclohexylidene, cycloheptylidene or 2-adamantylidene radical, X is the grouping —CH═CH—, an oxygen or a sulfur atom, and Y and Z, independently of one another, are each a methine group (CH) or a nitrogen atom, and their pharmaceutically acceptable addition salts with acids.

Individual compounds from that group that may be given special mention are:

(1) 4-[1-cyclohexylidene-1-(imidazolyl)-methyl]-benzonitrile,
(2) 4-[1-cyclopentylidene-1-(imidazolyl)-methyl]-benzonitrile,
(3) 4-[1-cycloheptylidene-1-(imidazolyl)-methyl]-benzonitrile,
(4) 4-[2-adamantylidene-1-(imidazolyl)-methyl]-benzonitrile,
(5) 4-[1-cyclohexylidene-1-(1,2,4-triazolyl)-methyl]-benzonitrile,
(6) 4-[1-cyclopentylidene-1-(1,2,4-triazolyl)-methyl]-benzonitrile,
(7) 4-[1-cycloheptylidene-1-(1,2,4-triazolyl)-methyl]-benzonitrile,
(8) 4-[2-adamantylidene-1-(1,2,4-triazolyl)-methyl]-benzonitrile,
(9) 4-[1-cyclohexylidene-1-(1,2,3-triazolyl)-methyl]-benzonitrile,
(10) 4-[1-cyclopentylidene-1-(1,2,3-triazolyl)-methyl]-benzonitrile,
(11) 5-[cyclohexylidene-1-imidazolylmethyl]-thiophene-2-carbonitrile.

(q) The compounds of Formula I as defined in DE-A-3 740 125. These are especially the compounds of Formula I

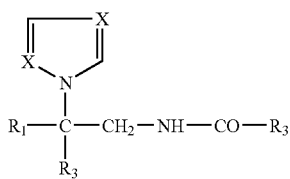

(I)

wherein X is CH or N, $R_1$ and $R_2$ are identical or different and are each phenyl or halophenyl, and $R_3$ is $C_1$-$C_4$ alkyl; $C_1$-$C_4$ alkyl substituted by CN, $C_1$-$C_4$ alkoxy, benzyloxy or by $C_1$-$C_4$ alkoxy-(mono-, di- or tri-)ethyleneoxy; $C_1$-$C_4$ alkoxy, phenyl; phenyl that is substituted by halogen or by cyano; a $C_5$-$C_7$ cycloalkyl group that is optionally condensed by benzene, or is thienyl, pyridyl or 2- or 3-indolyl; and acid addition salts thereof.

An individual compound from that group that may be given special mention is:

(1) 2,2-bis(4-chlorophenyl)-2-(1H-imidazol-1-yl)-1-(4-chlorobenzoyl-amino)ethane.

(®) The compounds of Formula I as defined in EP-A-293 978. These are especially the compounds of Formula I

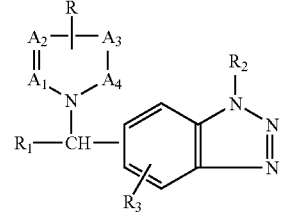

(I)

pharmaceutically acceptable salts and stereochemically isomeric forms thereof, wherein -$A_1$=$A_2$-$A_3$=$A_4$- is a divalent radical selected from —CH═N—CH═CH—, —CH═N—CH═N— and —CH═N—N═CH—, R is hydrogen or $C_1$-$C_6$ alkyl; $R_1$ is hydrogen, $C_1$-$C_{10}$ alkyl, $C_3$-$C_7$ cycloalkyl, $Ar_1$, $Ar_2$—$C_1'$-$C_6$ alkyl, $C_2$-$C_6$ alkenyl or $C_2$-$C_6$ alkynyl: $R_2$ is hydrogen; $C_1$-$C_{10}$ alkyl that is unsubstituted or substituted by $Ar_1$; $C_3$-$C_7$ cycloalkyl, hydroxy, $C_1$-$C_6$ alkoxy, $Ar_1$, $C_2$-$C_6$ alkenyl, $C_2$-$C_6$ alkynyl, $C_3$-$C_7$ cycloalkyl, bicyclo[2.2.1]heptan-2-yl, 2,3-dihydro-1H-indenyl, 1,2,3,4-tetrahydronaphthyl, hydroxy; $C_2$-$C_6$ alkenyloxy that is unsubstituted or substituted by $Ar_2$; $C_2$-$C_6$ alkynyloxy; pyrimidyloxy; di($Ar_2$) methoxy, (1-$C_1$-$C_4$ alkyl-4-piperidinyl)oxy, $C_1$-$C_{10}$ alkoxy; or $C_1$-$C_{10}$ alkoxy that is substituted by halogen, hydroxy, $C_1$-$C_6$ alkyloxy, amino, mono- or di-($C_1$-$C_6$ alkyl)amino, trifluoromethyl, carboxy, $C_1$-$C_6$ alkoxycarbonyl, Ar.sub.1, $Ar_2$—O—, $Ar_2$—S—, $C_3$-$C_7$ cycloalkyl, 2,3-dihydro-1,4-benzodioxinyl, 1H-benzimidazolyl, $C_1$-$C_4$ alkyl-substituted 1H-benzimidazolyl, (1,1'-biphenyl)-4-yl or by 2,3-dihydro-2-oxo-1H-benzimidazolyl; and $R_3$ is hydrogen, nitro, amino, mono- or di-($C_1$-$C_6$ alkyl)amino, halogen, $C_1$-$C_6$ alkyl, hydroxy or $C_1$-$C_6$ alkoxy; wherein $Ar_1$ is phenyl, substituted phenyl, naphthyl, pyridyl, aminopyridyl, imidazolyl, triazolyl, thienyl, halothienyl, furanyl, $C_1$-$C_6$ alkylfuranyl, halofuranyl or thiazolyl; wherein $Ar_2$ is phenyl, substituted phenyl or pyridyl; and wherein "substituted phenyl" is phenyl that is substituted by up to 3 substituents in each case selected independently of one another from the group consisting of halogen, hydroxy, hydroxymethyl, trifluoromethyl, $C_1$-$C_6$ alkyl, $C_1$-$C_6$ alkoxy, $C_1$-$C_6$ alkoxycarbonyl, carboxy, formyl, hydroxyiminomethyl, cyano, amino, mono- and di-($C_1$-$C_6$ alkyl)amino and nitro.

Individual compounds from that group that may be given special mention are:

(1) 6-[(1H-imidazol-1-yl)-phenylmethyl]-1-methyl-1H-benzotriazole,
(2) 6-[(4-chlorophenyl)(1H-1,2,4-triazol-1-yl)methyl]-1-methyl-1H-benzotriazole.

(s) The compounds of Formula II as defined in European Patent Publication No. EP-A-250 198, especially (1) 2-(4-chlorophenyl)-1,1-di(1,2,4-triazol-1-ylmethyl)ethanol,
(2) 2-(4-fluorophenyl)-1,1-di(1,2,4-triazol-1-ylmethyl)ethanol,
(3) 2-(2-fluoro-4-trifluoromethylphenyl)-1,1-di(1,2,4-triazol-1-ylmethyl)ethanol,
(4) 2-(2,4-dichlorophenyl)-1,1-di(1,2,4-triazol-1-ylmethyl) ethanol, (5) 2-(4-chlorophenyl)-1,1-di(1,2,4-triazol-1-ylmethyl)-ethanol,
(6) 2-(4-fluorophenyl)-1,1-di(1,2,4-triazol-1-yl-methyl) ethanol.

(t) The compounds of Formula I as defined in European Patent Publication No. EP-A-281 283, especially
(1) (1R*2R*)-6-fluoro-2-(4-fluorophenyl)-1,2,3,4-tetrahydro-1-(1H-1,2,4-triazol-1-methyl)naphthalene,
(2) (1R*,2R*)-6-fluoro-2-(4-fluorophenyl)-1,2,3,4-tetrahydro-1-(1H-imidazolylmethyl)-naphthalene,
(3) (1R*,2R*)- and (1R*,2S*)-2-(4-fluorophenyl)-1,2,3,4-tetrahydro-1-(1H-1,2,4-triazol-1-ylmethyl)naphthalene-6-carbonitrile,
(4) (1R*,2R*)- and (1R*,2S*)-2-(4-fluorophenyl)-1,2,3,4-tetrahydro-1-(1H-imidazolylmethyl)naphthalene-6-carbonitrile,
(5) (1R*,2R*)- and (1R*,2S*)-1,2,3,4-tetrahydro-1-(1H-1,2,4-triazol-1-ylmethyl)-naphthalene-2,6-dicarbonitrile,
(6) (1R*,2R*)- and (1R*,2S*)-1,2,3,4-tetrahydro-1-(1H-imidazol-1-ylmethyl)naphthalene-2,6-dicarbonitrile,
(7) (1R*,2S*)-2-(4-fluorophenyl)-1,2,3,4-tetrahydro-1-(5-methyl-1H-imidazolyl-methyl)naphthalene-6-carbonitrile.

(u) The compounds of Formula I as defined in European Patent Publication No. EP-A-296 749, especially
(1) 2,2'-[5-(1H-1,2,4-triazol-1-ylmethyl)-1,3-phenylene]di(2-methylpropiononitrile),
(2) 2,2'-[5-(imidazol-1-ylmethyl)-1,3-phenylene]di(2 methylpropiononitrile),
(3) 2-[3-(1-hydroxy-1-methylethyl)-5-(5H-1,2,4-triazol-1-ylmethyl)phenyl]-2-methylpropiononitrile,
(4) 2,2'-[5-dideuterio(1H-1,2,4-triazol-1-yl)methyl-1,3-phenylene]di(2-trideuteriomethyl-3,3,3-trideuteriopropiononitrile),
(5) 2,2'-[5-dideuterio(1H-1,2,4-triazol-1-yl)methyl-3-phenylene]di(2methylpropiononitrile).

(v) The compounds of Formula I as defined in European Patent Publication No. EP-A-299 683, especially
(1) (Z)-a-(1,2,4-triazol-1-ylmethyl)stilbene-4,4'-dicarbonitrile,
(2) (Z)-4'-chloro-a-(1,2,4-triazol-1-ylmethyl)stilbene-4-carbonitrile,
(3) (Z)-a-(1,2,4-triazol-1-ylmethyl)-4'-(trifluoromethyl)stilbene-4-carbonitrile,
(4) (E)-.beta.-fluoro-a-(1,2,4-triazol-1-ylmethyl)stilbene-4,4'-dicarbonitrile,
(5) (Z)-4'-fluoro-a-(imidazol-1-ylmethyl)stilbene-4-carbonitrile,
(6) (Z)-2',4'-dichloro-a-(imidazol-1-ylmethyl)stilbene-4-carbonitrile,
(7) (Z)-4'-chloro-a-(imidazol-1-ylmethyl)stilbene-4-carbonitrile,
(8) (Z)-a-(imidazol-1-ylmethyl)stilbene-4,4'dicarbonitrile,
(9) (Z)-a-(5-methylimidazol-1-ylmethyl)stilbene-4,4'-dicarbonitrile,
(10) (Z)-2-[2-(4-cyanophenyl)-3-(1,2,4-triazol-1-yl)propenyl]pyridine-5-carbonitrile.

(w) The compounds of Formula I as defined in European Patent Publication No. EP-A-299 684, especially
(1) 2-(4-chlorobenzyl)-2-fluoro-1,3-di(1,2,4-triazol-1-yl) propane,
(2) 2-fluoro-2-(2-fluoro-4-chlorobenzyl)-1,3-di(1,2,4-triazol-1-yl)propane,
(3) 2-fluoro-2-(2-fluoro-4-trifluoromethylbenzyl)-1,3-di(1,2,4-triazol-1-yl)propane,
(4) 3-(4-chlorophenyl)-1-(1,2,4-triazol-1-yl)-2-(1,2,4-triazol-1-ylmethyl)butan-2-ol,
(5) 2-(4-chloro-a-fluorobenzyl)-1,3-di(1,2,4-triazol-1-yl) propan-2-ol,
(6) 2-(4-chlorobenzyl)-1,3-bis(1,2,4-triazol-1-yl)propane,
(7) 4-[2-(4-chlorophenyl)-1,3-di(1,2,4-triazol-1-ylmethyl) ethoxymethyl]-benzonitrile,
(8) 1-(4-fluorobenzyl)-2-(2fluoro-4-trifluoromethylphenyl)-1,3-di(1,2,4-triazol-1-yl)-propan-2-ol,
(9) 2-(4-chlorophenyl)-1-(4-fluorophenoxy)-1,3-di(1,2,4-triazol-1-yl)propan-2-ol,
(10) 1-(4-cyanobenzyl)-2-(2,4-difluorophenyl)-1,3di(1,2,4-triazol-1-yl)propan-2-ol,
(11) 2-(4-chlorophenyl)-1-phenyl-1,3-di(1,2,4-triazol-1-yl) propan-2-ol.

(x) The compounds as defined in claim 1 of European Patent Publication No. EP-A-316 097, especially
(1) 1,1-dimethyl-8-(1H-1,2,4-triazol-1-ylmethyl)-2(1H)-naphtho[2,1-b]furanone,
(2) 1,2-dihydro1,1-dimethyl-2-oxo-8-(1H-1,2,4-triazol-1-ylmethyl)naphtho[2,1-b]-furan-7-carbonitrile,
(3) 1,2-dihydro-1,1-dimethyl-2-oxo-8-(1H-1,2,4-triazol-1-ylmethyl)naphtho[2,1-b]-furan-7-carboxamide,
(4) 1,2-dihydro-1,1-dimethyl-2-oxo-8-[di(1H-1,2,4-triazol-1-yl)methyl]naphtho[2,1-b]-furan-7-carbonitrile.

(y) The compounds of Formula I as defined in European Patent Publication No. EP-A-354 689, especially
(1) 4-[2-(4-cyanophenyl)-3-(1,2,4-triazol-1-yl)propyl]benzonitrile,
(2) 4-[1-(4-chlorobenzyl)-2-(1,2,4-triazol-1-yl)ethyl]benzonitrile,
(3) 4-[2-(1,2,4-triazol-1-yl)-1-(4-trifluoromethyl]benzyl) ethyl]benzonitrile,
(4) 4-[2-(1,2,4-triazol-1-yl)-1-(4-[trifluoromethoxy]benzyl) ethyl]benzonitrile.

(z) The compounds of formula (1) as defined in European Patent Publication No. EP-A-354 683, especially
(1) 6-[2-(4-cyanophenyl)-3-(1,2,4-triazol-1-yl)-propyl]nicotinonitrile,
(2) 4-[1-(1,2,4-triazol-1-yl-methyl)-2-(5-[trifluoromethyl] pyrid-2-yl)ethyl]benzonitrile.

Examples of steroidal aromatase inhibitors that may be mentioned are:

(aa) The compounds of Formula I as defined in European Patent Publication No. EP-A-181 287. These are especially the compounds of Formula I

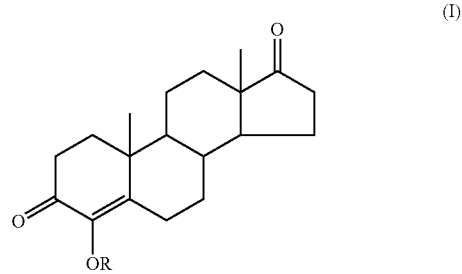

(I)

wherein R is hydrogen, acetyl, heptanoyl or benzoyl.
An individual compound from that group that may be given special mention is:
(1) 4-hydroxy-4-androstene-3,17-dione.

(ab) The compounds as defined in the claims of U.S. Pat. No. 4,322,416, especially 10-(2-propynyl)-oestr-4-ene-3,17-dione.

(ac) The compounds as defined in the claims of German Patent Application No. DE-A-3 622 841, especially 6-methyleneandrosta-1,4-diene-3,17-dione.

(ad) The compounds as defined in the claims of Published British Patent Application No. GB-A-2 17 1100, especially 4-amino-androsta-1,4,6-triene-3,17-dione.

(ae) The compound androsta-1,4,6-triene-3,17-dione.

The content of the patent applications mentioned under (a) to (z) and (aa) to (ad), especially the subgroups of compounds disclosed therein and the individual compounds disclosed therein as examples, are incorporated by reference into the disclosure of the present application.

The general terms used hereinbefore and hereinafter to define the compounds have the following meanings:

Organic radicals designated by the term "lower" contain up to and including 7, preferably up to and including 4, carbon atoms.

Acyl is especially a lower alkanoyl.

Aryl is, for example, phenyl or 1- or 2-naphthyl, each of which is unsubstituted or substituted by lower alkyl, hydroxy, lower alkoxy, lower alkanoyloxy, amino, lower alkylamino, di-lower alkylamino, lower alkanoylamino or by halogen.

Pharmaceutically acceptable salts of the above-mentioned compounds are, for example, pharmaceutically acceptable acid addition salts or pharmaceutically acceptable metal or ammonium salts.

Pharmaceutically acceptable acid addition salts are especially those with suitable inorganic or organic acids, for example strong mineral acids, such as hydrochloric acid, sulfuric acid or phosphoric acid, or organic acids, especially aliphatic or aromatic carboxylic or sulfonic acids, for example formic, acetic, propionic, succinic, glycolic, lactic, hydroxysuccinic, tartaric, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, p-toluenesulfonic, naphthalenesulfonic, sulfanilic or cyclohexylsulfamic acid; or with other acidic organic substances, for example ascorbic acid.

Pharmaceutically acceptable salts may also be formed, for example, with amino acids, such as arginine or lysine. Compounds containing acid groups, for example a free carboxy or sulfo group, can also form pharmaceutically acceptable metal or ammonium salts, such as alkali metal or alkaline earth metal salts, for example sodium, potassium, magnesium or calcium salts, or ammonium salts derived from ammonia or suitable organic amines. Also under consideration are especially aliphatic, cycloaliphatic, cycloaliphatic-aliphatic or araliphatic primary, secondary or tertiary mono-, di- or polyamines, such as lower alkylamines, for example di- or triethylamine, hydroxy-lower alkylamines, for example 2-hydroxyethylamine, bis(2-hydroxyethyl)amine or tris(2-hydroxyethyl)amine, basic aliphatic esters or carboxylic acids, for example 4-aminobenzoic acid 2-diethylaminoethyl ester, lower alkyleneamines, for example 1-ethylpiperidine, cycloalkylamines, for example dicyclohexylamine, benzylamines, for example N,N'-dibenzylethylenediamine; also heterocyclic bases, for example of the pyridine type, for example pyridine, collidine or quinoline. If several acidic or basic groups are present, mono- or poly-salts can be formed. Compounds according to the invention having an acidic and a basic group may also be in the form of internal salts, i.e., in the form of zwitterions and another part of the molecule in the form of a normal salt.

In the case of the above-mentioned individual compounds the pharmaceutically acceptable salts are included in each case insofar as the individual compound is capable of salt formation.

The compounds listed, including the individual compounds mentioned, both in free form and in salt form, may also be in the form of hydrates, or their crystals may include, for example, the solvent used for crystallization. The present invention relates also to all those forms.

Many of the above-mentioned compounds, including the individual compounds mentioned, contain at least one asymmetric carbon atom. They can, therefore, occur in the form of R- or S-enantiomers and as enantiomeric mixtures thereof, for example in the form of a racemate. The present invention relates to the use of all those forms and to the use of all further isomers, and of mixtures of at least 2 isomers, for example mixtures of diastereoisomers or enantiomers which can occur when there are one or more further asymmetric centres in the molecule. Also included are, for example, all geometric isomers, for example cis- and trans-isomers, that can occur when the compounds contain one or more double bonds.

In another embodiment of the invention, pharmaceutical compositions can be prepared for use in the invention. The pharmaceutical compositions according to the invention are compositions for enteral, such as peroral or rectal administration, also for transdermal or sublingual administration, and for parenteral, for example intravenous, subcutaneous and intramuscular, administration. Suitable unit dose forms, especially for peroral and/or sublingual administration, for example dragees, tablets or capsules, comprise preferably from approximately 0.01 mg to approximately 20 mg, especially from approximately 0.1 mg to approximately 10 mg, of one or more of the above-mentioned compounds, or of pharmaceutically acceptable salts thereof, together with pharmaceutically acceptable carriers. The particularly preferred form of administration is oral.

The proportion of active ingredient in such pharmaceutical compositions is generally from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticizer, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilizers. In soft capsules, the active ingredient is preferably dissolved or suspended in suitable oily excipients, such as fatty oils, paraffin oil or liquid polyethylene glycols, to which stabilizers and/or anti-bacterial agents may also be added. There may also be used capsules that are easily bitten through, in order to achieve by means of the sublingual ingestion of the active ingredient that takes place as rapid an action as possible.

Suitable rectally or transvaginally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilizers.

Dyes or pigments may be added to the pharmaceutical compositions, especially to the tablets or dragee coatings, for example for identification purposes or to indicate different doses of active ingredient.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragee cores.

Although the invention has been described in terms of specific embodiments and applications, persons skilled in the art may, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A method of preparing a pre-menopausal female patient for a surgical ablation or resection procedure on the endometrium of the patient's uterus, the method comprising the step of thinning the endometrium by administering to the patient one or more doses of a pharmaceutical composition consisting of one or more third generation aromatase inhibitors selected from the group consisting of anastrozole, letrozole, vorozole and exemestane, said aromatase inhibitors having in vitro IC50 values of 10-5 M or lower, in a pharmaceutically acceptable carrier in an amount effective to produce thinning of the patient's endometrium.

2. The method of claim 1 wherein the surgical ablation or resection procedure is selected from the group consisting of endometrial ablation, endometrial resection, endometrial ablation with electrocautery (e.g., roller ball electrode), endometrial laser resection, balloon thermal ablation, microwave endometrial ablation, endometrial thermal hydroablation, and tubal cannulation.

3. The method of claim 1 wherein from 1 to 10 daily doses of the aromatase inhibitor are administered.

4. The method of claim 3 wherein about 10 daily doses are administered.

5. The method of claim 1 wherein the daily doses are administered from 1 to 30 days prior to performing the procedure.

6. The method of claim 1 wherein the endometrium is thinned to less than 6 mm, and preferably less than 4 mm, as measured from the subendometrium interface with the endometrium.

7. The method of claim 1 wherein the aromatase inhibitor is letrozole and is administered in a daily dose of from about 2.5 mg to about 50 mg.

8. The method of claim 1 wherein the aromatase inhibitor is anastrozole and is administered in a daily dose of from about 1 mg to about 20 mg.

9. The method of claim 1 wherein the aromatase inhibitor is vorozole and is administered in a daily dose of from about 4 mg to about 40 mg.

10. The method of claim 1 wherein the aromatase inhibitor is exemestane and is administered in a daily dose of from about 25 mg to about 250 mg.

11. The method of claim 1 wherein the aromatase inhibitor is selected from aromatase inhibitors having a half-life of about 8 hours to about 4 days.

12. The method of claim 11 wherein the aromatase inhibitor is selected from aromatase inhibitors having a half-life of about 2 days.

13. The method of claim 1 wherein the aromatase inhibitor is administered orally.

14. The method of claim 1 wherein the amount of aromatase inhibitor is selected from amounts effective to prevent endometrial proliferation and to cause disruption of the endometrium and its breakdown and consequent thinning.

15. The method of claim 1 wherein the pharmaceutical composition includes another therapeutic agent.

16. The method of claim 15 wherein the another agent is a steroid or antisteroid.

17. The method of claim 16 wherein the therapeutic agent is a hormone.

* * * * *